United States Patent [19]

Franklin et al.

[11] 4,282,013
[45] Aug. 4, 1981

[54] VACUUM PUMP OPERATION IN A MALEIC ANHYDRIDE RECOVERY SYSTEM

[75] Inventors: Frederick C. Franklin, Pinole; Stephen G. Paradis, Fairfax, both of Calif.

[73] Assignee: Chevron Research Company, San Francisco, Calif.

[21] Appl. No.: 851,248

[22] Filed: Nov. 14, 1977

[51] Int. Cl.³ ............................................. B01D 19/00
[52] U.S. Cl. ........................................ 55/48; 55/51; 55/55; 260/346.76
[58] Field of Search ..................... 55/48, 51, 55, 89; 141/7, 8; 260/346.76

[56] References Cited

U.S. PATENT DOCUMENTS

| | | | |
|---|---|---|---|
| 2,574,644 | 11/1951 | Landau | 55/48 X |
| 3,045,716 | 7/1962 | Morgan et al. | 55/48 X |
| 3,261,847 | 7/1966 | Sullivan | 260/346.76 X |
| 3,818,680 | 6/1974 | Marquis | 55/48 |
| 3,891,680 | 6/1975 | Katsumoto et al. | 55/48 X |
| 3,965,123 | 6/1976 | Franklin | 260/346.76 |

*Primary Examiner*—Robert H. Spitzer
*Attorney, Agent, or Firm*—D. A. Newell; T. G. DeJonghe; C. J. Caroli

[57] ABSTRACT

In a reduced-pressure process for distilling crude maleic anhydride recovered by separation from an organic absorbent wherein reduced pressure is obtained using a liquid ring-seal vacuum pump, the improvement which comprises sealing the liquid ring-seal vacuum pump by circulating a maleic anhydride absorbent from a regenerating zone through the vacuum pump chamber.

1 Claim, 2 Drawing Figures

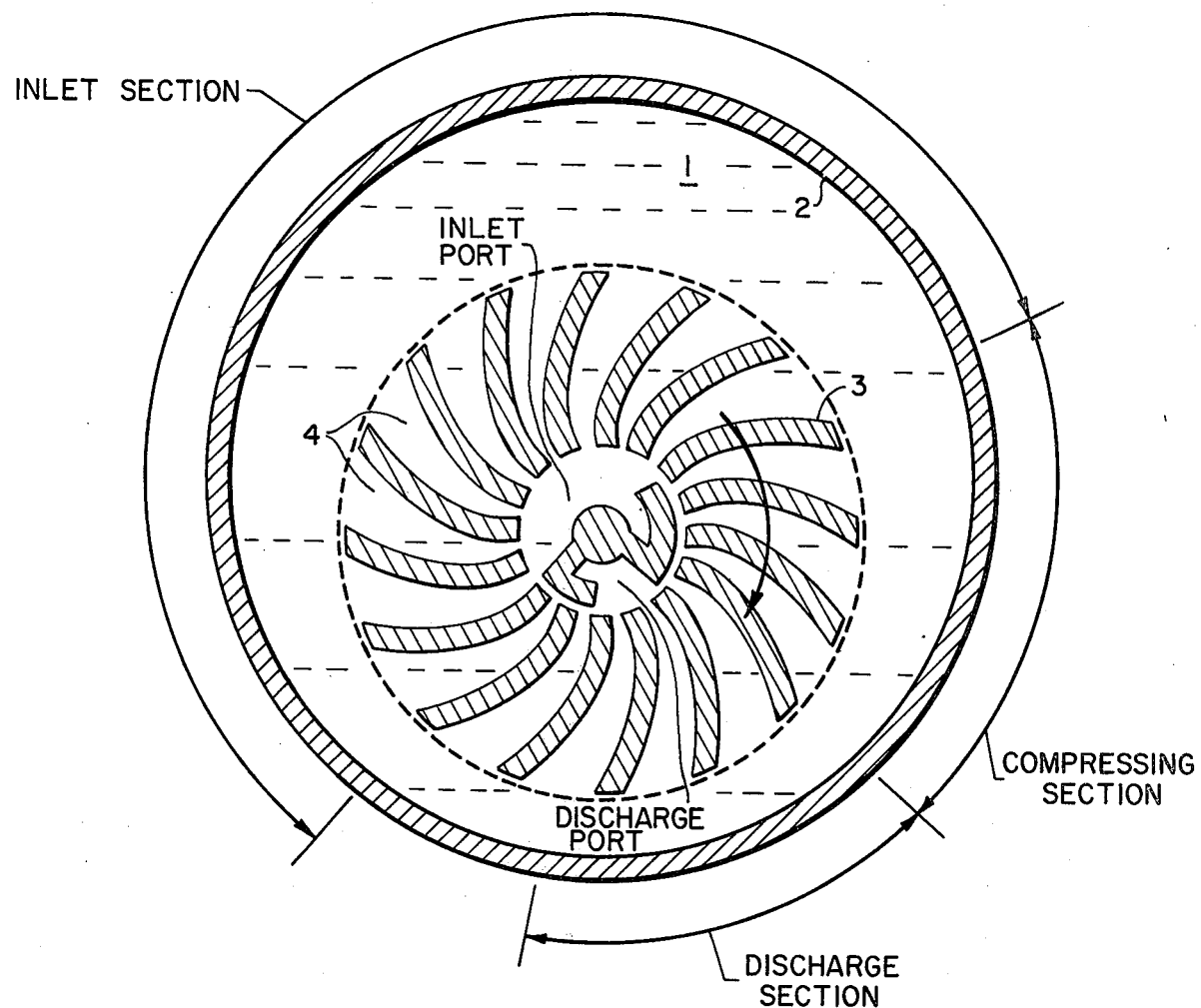
FIG.—1.

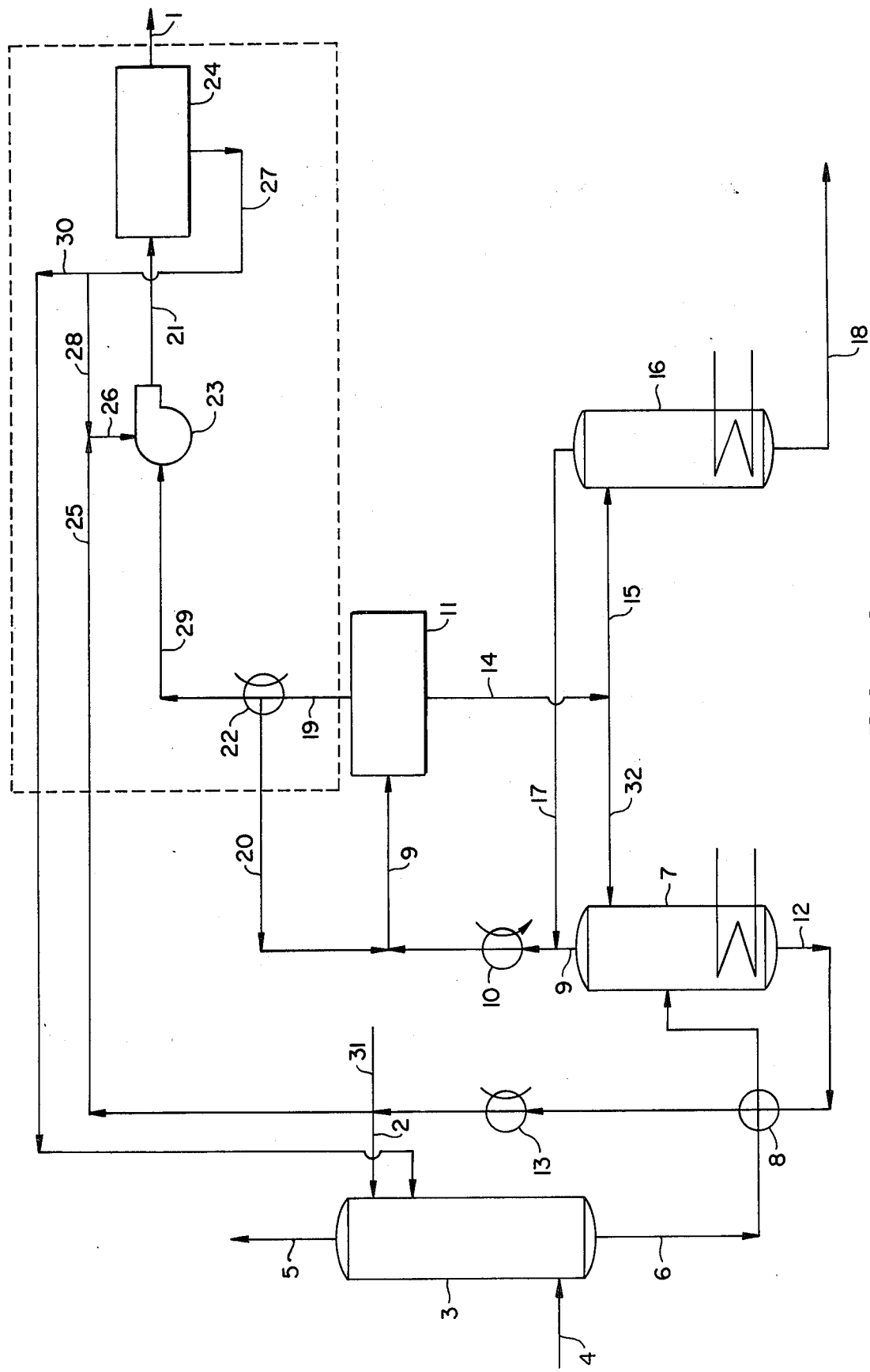
FIG._2.

VACUUM PUMP OPERATION IN A MALEIC ANHYDRIDE RECOVERY SYSTEM

BACKGROUND OF THE INVENTION

This invention concerns an improved method for sealing liquid ring-type vacuum pumps used to maintain reduced pressure during distillation of crude maleic anhydride.

Maleic anhydride is conventionally produced by the vapor phase oxidation of hydrocarbon feedstocks. Crude anhydride can be recovered from the oxidation product by absorption into an organic solvent followed by reduced pressure distillation of the anhydride-rich absorbent. The distilled crude maleic anhydride is taken overhead and the anhydride-lean absorbent bottoms are recycled to the absorber. A portion of the crude maleic anhydride is recycled to the distillation vessel and the balance is charged to a lights stripper, also operated at reduced pressure. In the lights stripper low boiling contaminants are distilled overhead. Some maleic anhydride is carried over with the low boiling impurities. Accordingly, as used herein, the term "anhydride distillation system" includes the distillation of anhydride-rich absorbent to obtain a crude anhydride product and the distillation of the crude product to strip low-boiling contaminants.

In conventional process designs, the anhydride distillation system is maintained at reduced-pressure by a vacuum system which includes a vacuum pump or pumps connected to the distillation system through condensers. Vacuum pumps are preferred because when steam jets are used, sufficient water travels back up the feed line to hydrolyze carried over maleic anhydride to solid, insoluble acid, which then can cause severe plugging problems. In addition, any product passing to the jets is lost to further product recovery. Thus, vacuum pumps connected through condensers are preferred over steam jets.

In spite of the use of condensers in the vacuum system, some organic material may collect and foul some moving parts of reciprocating type vacuum pumps. In addition, unless after condensers are provided, maleic anhydride vapor discharged from reciprocating-type vacuum pumps would be lost from the recovered product. Even in liquid ring seal type vacuum pumps, recovered product may foul the sealant if the sealant is not properly selected to provide adequate solubility for absorbed products and is not continuously treated to remove them. Accordingly, it would be advantageous to provide a method which minimizes pump fouling and at the same time increases recovery of product.

SUMMARY OF THE INVENTION

It has now been found that pump fouling in a reduced pressure anhydride distillation system, caused by precipitated organic material, can be essentially eliminated while increasing product recovery by using liquid ring-seal-type vacuum pumps and employing a maleic anhydride absorbent as the sealing liquid.

BRIEF DESCRIPTION OF THE DRAWING

The following detailed description of the invention refers to the accompanying drawings in which:

FIG. 1 illustrates a liquid ring-seal vacuum pump, and,

FIG. 2 schematically illustrates a maleic anhydride plant design employing a liquid ring-seal vacuum pump sealed in accordance with the invention.

DETAILED DESCRIPTION OF THE INVENTION

This invention concerns an improved vacuum system for reduced pressure distillation of a maleic anhydride-rich organic absorbent and the crude anhydride product. In particular, it has been found that vacuum pump fouling can be eliminated by using a liquid ring-seal type vacuum pump and a liquid maleic anhydride absorbent sealant, which after use, is recirculated to an absorbent regeneration zone for further product recovery.

U.S. Pat. No. 3,818,680 thoroughly describes the recovery of maleic anhydride from a gaseous mixture by contacting the mixture with an organic solvent to absorb the anhydride, and then distilling the anhydride-rich absorbent under reduced pressure. U.S. Pat. Nos. 2,574,644; 3,040,059; 2,893,924 and 3,891,680 describe similar processes using various other organic absorbents. In each of these disclosed processes, the anhydride is separated from the absorbent in a regenerating zone by distillation, usually at reduced pressure maintained by a vacuum system using a vacuum pump or pumps.

Among other factors, this invention is based upon the discovery that vacuum pump fouling in the anhydride distillation system can be minimized and product recovery can be increased by feeding absorbent into the pump chamber of a liquid ring-seal-type vacuum pump and withdrawing a small stream of anhydride-rich absorbent from the separator of the vacuum system for removal of absorbed product in an absorbent regenerator. Sealing the vacuum pump in this manner prevents organic material from fouling the pump chamber, and increases product recovery.

Liquid ring-seal vacuum pumps are well-known, commercially available vacuum pumps. In general, they operate using a balanced rotor as the only moving part. Referring to FIG. 1, an example of a ring-seal vacuum pump operates using a rotating ring of liquid 1 following a path around the interior of the vacuum pump body 2. Power to keep the liquid rotating is supplied by rotor 3. The axis of rotor 3 is offset from the body axis so that as rotor 3 revolves the liquid 1 fills, then empties each rotor chamber 4 during a single revolution. Thus, in the inlet section the liquid moves outwardly, drawing gas from the inlet port into the rotor chambers; in the compressing section liquid moves inwardly, compressing gas in the rotor chambers; and in the discharge section, compressed gas is exhausted from the discharge port. In this way, a vacuum is created, setting up a pumping action.

Referring to FIG. 2, which illustrates a preferred embodiment of the invention, unit 3 is an absorption column, preferably having about 30 plates, and unit 7 is a reduced pressure, absorbent regenerator column. In a continuous mode of operation, the maleic anhydride-containing gaseous feed is introduced into the absorption column 3 at a point below the bottom tray via line 4 and flows upward. A liquid organic absorbent is introduced into the absorption column 3 at a point above the top tray via line 2. Thus, the gas feed and liquid absorbent streams pass in countercurrent flow. Maleic anhydride is absorbed and the anhydride-rich absorbent passes from the column 3 via line 6. Residual gas, containing water, carbon dioxide, and unoxidized hydrocarbon components is vented via line 5.

Typically, the anhydride-rich absorbent contains from 10 to 30 weight percent anhydride. After being withdrawn from the absorption unit 3, it is introduced into a reduced-pressure absorbent regenerator column 7 through heat exchanger 8. In column 7 maleic anhydride is separated from the absorbent by fractional distillation. Maleic anhydride is separated as an overhead vapor and condensed by means of heat exchanger 10 and directed via line 9 to the reflux drum 11 which is maintained at reduced pressure. Anhydride-lean absorbent is withdrawn as a bottoms product and recycled to absorption column 3 via line 12. The recycled absorbent is passed through exchanger 8 and serves as a convenient source of heat energy. This also serves to cool the recycled absorbent. Absorbent may be further cooled to the required absorber temperature, if necessary, by cooler 13.

Liquid maleic anhydride is withdrawn from drum 11 via line 14, a portion is recycled to absorbent regenerator column 7 via line 32 and the balance is passed to lights stripper 16 via line 15. In stripper 16, low boiling impurities are separated as an overhead vapor and recycled via lines 17 and 9 to reflux drum 11. Refined maleic anhydride is recovered as a bottoms product via line 18.

The absorbent regenerator column and lights stripper are operated at reduced pressure. The reduction in pressure required for the distillation system is effected via line 19 and associated lines 29 and 21 by the vacuum system shown within the dotted-line area. This invention particularly concerns the vacuum system as represented by condenser 22, pump 23, and separator 24, and its interconnection with the absorbent system represented by absorber 3, and absorbent regenerator 7.

Vapors collecting in reflux drum 11 are withdrawn from the drum and enter the vacuum system via line 19. The vapor comprises minor amounts of maleic anhydride as well as other contaminants such as acetic and acrylic acids from the lights stripper overhead. Despite passing through condenser 22 some of the organic materials in line 19 pass to vacuum pump 23 via line 29 and in a vacuum system of conventional design could precipitate out of the vapor, fouling the pump, or pass to the vent without further product recovery. It has been found that the fouling problem can be eliminated and product recovery increased by sealing a liquid ring-seal type vacuum pump with absorbent which is continuously regenerated. Thus, referring to the schematic, a small amount of anhydride absorbent is withdrawn from line 31 (makeup absorbent) or 12 (regenerated absorbent) and is fed to the liquid ring-seal vacuum pump via lines 25 and 26, together with a larger recirculated sealant stream from separator 24 via lines 28 and 26. The absorbent-sealant maintains in solution any organic material absorbed and flows down the vacuum line 21 into separator 24 from which it is returned to the absorption column 3 via lines 27 and 30. In this way, not only is the vacuum system kept in running condition, but as an additional benefit the maleic anhydride vaporizing out of the reflux drum into the vacuum system is recovered. As much as 1% of the total maleic anhydride recovered from the absorber is salvaged by this process.

Maleic anhydride absorbents which are suitable for use in the present invention are well known in the art. For example, U.S. Pat. No. 2,574,644 discloses the use of dibutyl phthalate for the recovery of maleic anhydride from an oxidation reactor effluent stream; U.S. Pat. No. 2,893,924 discloses the use of diphenylpentachloride absorbent as well as tricresyl phosphate as an absorbent for removing maleic anhydride by absorption; U.S. Pat. No. 3,040,095 discloses the use of molten wax as an absorbent for removing maleic anhydride from an oxidation reactor effluent stream; U.S. Pat. No. 3,818,680 discloses alkyl or alkenyl succinic anhydrides, in general and for molecular carboxylic acid anhydrides, as absorbents for the removal of maleic anhydride from gas streams; and U.S. Pat. No. 3,891,680 discloses the use of certain dialkyl phthalates as absorbents for removing maleic anhydride from gas streams containing maleic anhydride. The disclosures of U.S. Pat. Nos. 3,891,680 and 3,818,860, especially in that they relate to the use of organic absorbents for maleic anhydride removal, are incorporated herein by reference. In general, suitable maleic anhydride absorbents are those which remain in the liquid phase when used in high-temperature distillations to prevent carry-over loss and also to prevent losses when distilling off the lower-boiling maleic anhydride in subsequent purification and which have a high solubility for maleic anhydride.

The following example further illustrates the advantages of the invention and suggests additional embodiments within the scope of the following claims.

EXAMPLE 1

This example was calculated from values obtained by laboratory experiments and from a knowledge of liquid ring-seal vacuum pumps. Parts are by weight unless noted otherwise.

Referring to FIG. 2, which is a block flow diagram of a maleic anhydride plant, the oxidizer off-gases are scrubbed in the absorber column 3 with a solvent for maleic anhydride. The maleic anhydride rich absorbent is then passed into an absorbent regenerator 7 wherein the maleic anhydride vapor, is removed by distillation. It is then condensed and passed into a reflux drum 11 maintained at 190° F. and under 27 mm of mercury pressure. Liquid maleic anhydride is kept in the reflux drum as a supply for controlling reflux. The low-boiling, volatile materials in the reflux drum are removed, along with a considerable amount of maleic anhydride, through line 19. These vapors pass through a condenser 22 operated at 125° F., wherein some of the maleic anhydride is condensed and returned to the reflux drum via line 20. The remainder of the vapor, at 212 parts per hour and containing 14 percent (30 parts) of maleic anhydride, passes through line 29 into the liquid ring-seal vacuum pump 23. At the same time, maleic anhydride lean absorbent from the absorbent regenerator 7 at 2000 parts per hour in line 25 and recycle absorbent from the separator 24 at 28,000 parts per hour in line 28 are combined and charged to the chamber of liquid ring-seal vacuum pump 23 via line 26 to lubricate and maintain vacuum. The exhaust from this pump is passed via line 21, into a separator 24, wherein the liquid absorbent settles out and is removed via line 27. This absorbent stream 27 is then divided into two portions, one portion recycling to pump 23 via line 28, the other portion, at 2030 parts per hour and containing about 0.7% (15 parts) of maleic anhydride, is recycled back to the absorption column 3 via line 30. The vent line 1 from the separator 24 removes 183 parts per hour of disposables, including 15 parts per hour of maleic anhydride and 1 part per hour of absorbent. Thus the incorporation of this method of operating the liquid ring-seal vacuum pump effects recovery of 50% (15 parts per hour) of the maleic anhydride, which would otherwise pass out the vent to disposal.

What is claimed is:

1. A method for increasing the yield and reducing mechanical vacuum pump fouling from precipitated maleic anhydride in a continuous process for preparing maleic anhydride by vapor phase oxidation of a hydrocarbon feedstock followed by absorption of the maleic anhydride by a liquid organic absorbent therefor in an absorption zone and then stripping of the maleic anhydride from the organic absorbent under reduced pressure conditions, wherein a mechanical vacuum pump means is employed to develop said reduced pressure conditions in said stripping zone of said process, the improvement in recovery of residual maleic anhydride which comprises:

(a) flowing vapors containing said residual maleic anhydride from said stripping zone to the central portion of a liquid-ring seal vacuum pump constituting said mechanical pump means;

(b) concurrently flowing at least a portion of said stripped organic absorbent into the circumferential ring portion of said liquid-ring seal vacuum pump to form the liquid-ring seal and working liquid of said pump;

(c) continuously mixing said vapors with said stripped organic absorbent to form a liquid maleic anhydride-rich organic absorbent phase and a gaseous disposables phase;

(d) withdrawing the resultant liquid maleic anhydride-rich organic absorbent phase and reduced gaseous disposables phase from said pump;

(e) separating said gaseous disposables phase from said liquid maleic anhydride-rich organic absorbent phase and venting said separated gaseous disposables phase;

(f) passing a portion of said liquid maleic anhydride-rich organic absorbent phase to said absorption zone of said process to recycle said maleic anhydride;

(g) passing the remainder of said liquid maleic anhydride-rich organic absorbent phase into the circumferential ring portion of said pump to maximize the concentration of maleic anhydride therein;

whereby said method substantially eliminates vapor phase maleic anhydride from said gaseous disposables phase and from contact with portions of said mechanical vacuum pump exposed to ambient atmospheric conditions.

* * * * *